United States Patent [19]

Ifflaender et al.

[11] Patent Number: 5,065,762
[45] Date of Patent: Nov. 19, 1991

[54] EXTRACORPOREAL LITHOTRIPSY APPARATUS FOR THE DISINTEGRATION OF CALCULI HAVING AN UNATTENUATED LOCATING FIELD

[75] Inventors: Helmut Ifflaender, Spardorf; Eike Matura; Walter Polster, both of Erlangen; Manfred Rattner, Grossenseebach, all of Fed. Rep. of Germany

[73] Assignee: Siemens Aktiengesellschaft, Munich, Fed. Rep. of Germany

[21] Appl. No.: 527,438

[22] Filed: May 23, 1990

[30] Foreign Application Priority Data

Jun. 2, 1989 [EP] European Pat. Off. ......... 89110039

[51] Int. Cl.⁵ ............................................. A61B 17/22
[52] U.S. Cl. ........................... 128/660.03; 128/24 EL
[58] Field of Search .............. 128/660.03, 24 EL; 378/99, 147, 154

[56] References Cited

U.S. PATENT DOCUMENTS

| | | | |
|---|---|---|---|
| 4,771,787 | 9/1988 | Wurster et al. | 128/660.03 |
| 4,879,993 | 11/1989 | Reichenberger et al. | 128/660.03 |
| 4,915,114 | 4/1990 | Hassler | 128/660.03 |
| 4,928,672 | 5/1990 | Grasser et al. | 128/660.03 |
| 4,957,099 | 9/1990 | Hassler | 128/660.03 |
| 4,984,565 | 1/1991 | Rattner et al. | 128/24 EL |

FOREIGN PATENT DOCUMENTS 0316863 5/1989 European Pat. Off. .
3727692 3/1989 Fed. Rep. of Germany .

Primary Examiner—Ruth S. Smith
Attorney, Agent, or Firm—Hill, Van Santen, Steadman & Simpson

[57] ABSTRACT

A shock wave source of the type suitable for treating calculi in the body of a patient has a closed space filled out by a coupling fluid, as well as a hollow-cylindrical, air-filled space, centrally located in the shock wave head, which does not attenuate x-rays. The centrally located space allows for acceptance of an ultrasound locating system. It is covered on the application side by a flexible foil, providing for a shock wave head which is free from contamination of particles from the opening of the above mentioned space to the application surface of the patient.

4 Claims, 1 Drawing Sheet

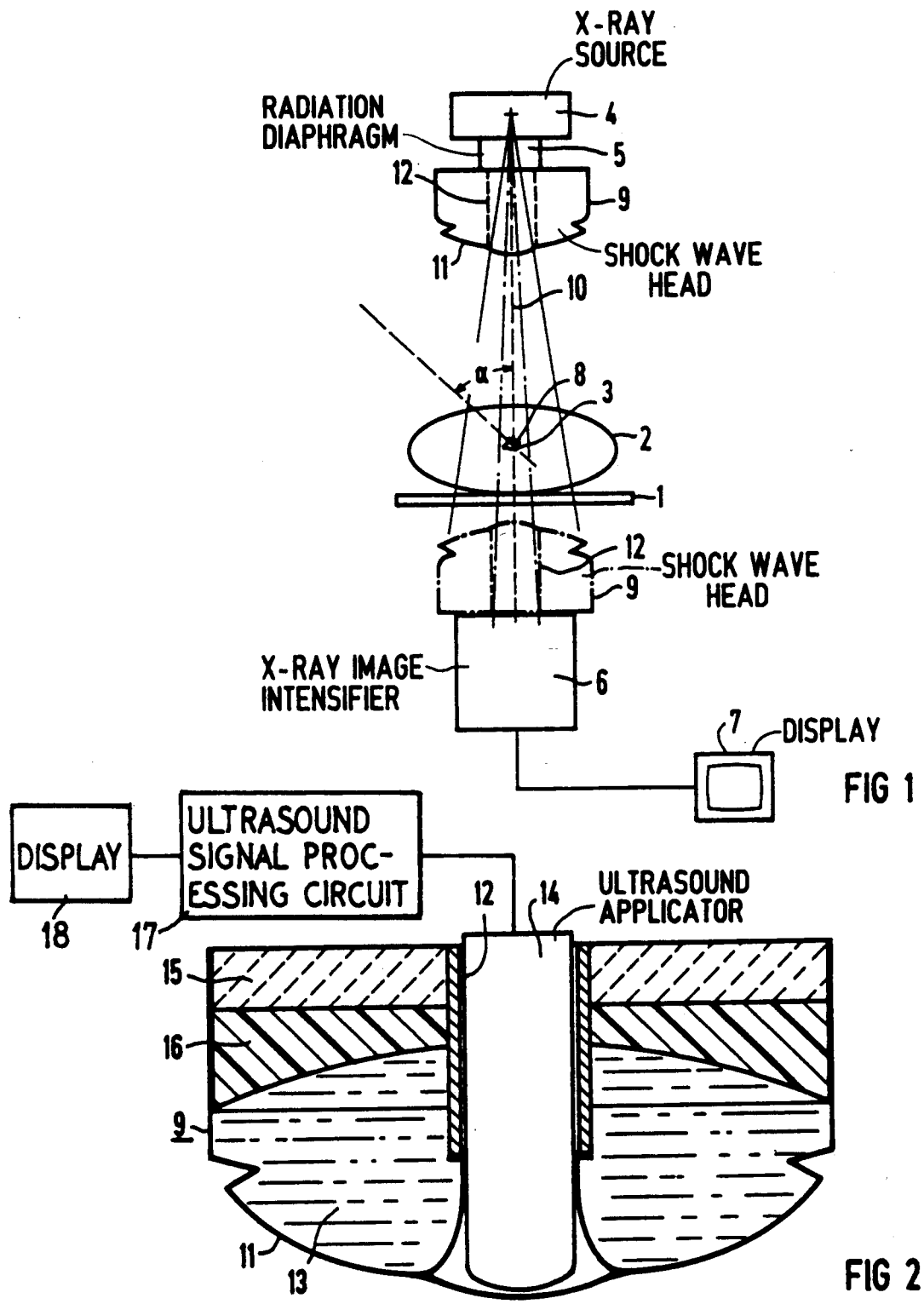

EXTRACORPOREAL LITHOTRIPSY APPARATUS FOR THE DISINTEGRATION OF CALCULI HAVING AN UNATTENUATED LOCATING FIELD

BACKGROUND OF THE INVENTION

1. Field of the Invention

The present invention is related to an extracorporeal lithotripsy apparatus, having an ultrasound generator for generating a pressure wave, which may be focused to disintegrate calculi in a patient.

2. Description of Prior Art

The disintegration of calculi by the use of a lithotripsy apparatus is achieved by emitting shock waves focused on calculi in vivo. The shock waves are focused by a determination of the focal range, within which the shock waves must be directed in order to disintegrate calculi in a patient. The focal range, necessary to focus a pressure wave capable of disintegrating the calculi, is determined by either an x-ray system, having an x-ray radiator and radiation receiver, or an ultrasound locating system. The ultrasound system is centrally located in the shock wave head, so that the central rays of the ultrasound system and the shock wave head coincide. An x-ray system may be used for initially locating the position of calculi, and an ultrasound system is preferred for determining subsequent changes in the locations of calculi during treatment. Under these circumstances it is preferable, to arrange the ultrasound locating system within the shock wave head so that it is removable, allowing the central region of the shock wave head to be further employed for the unattenuated transmission of x-rays.

A device which permits removal of the ultrasound locating system from the center of the shock wave head, while preventing the coupling fluid from running out, is disclosed in EP-A-0316863. A hollow-cylindrical air-filled space, which limits the space filled with coupling fluid, and does not attenuate x-rays, is provided for acceptance of the ultrasound system within the center of the shock wave head. This space is exposed (open) on the application side, and thus permits contamination of the space to occur.

SUMMARY OF THE INVENTION

It is an object of the present invention to further improve the initially recited shock wave source by providing a shock wave head, such that x-rays are not attenuated when passing through the space provided to accept the ultrasound locating system, and contamination of this space from exposure to the patient along the application surface is eliminated.

This object is achieved is accordance with the principles of the present invention in extracorporeal lithotripsy apparatus having a flexible foil disposed at the application side of the space provided for the ultrasound locating system.

DESCRIPTION OF THE DRAWINGS

FIG. 1 is a cross-sectional view of lithotripter constructed in accordance with the principles of the present invention, disposed adjacent to a patient and demonstrating the use of x-rays through the center of the shock wave head for locating calculi within the patient.

FIG. 2 is a cross-sectional view of a lithotripter, constructed in accordance with the principles of the present invention, demonstrating the use of an ultrasound locating system in conjunction therewith.

DESCRIPTION OF THE PREFERRED EMBODIMENTS

A shock wave head constructed in accordance with the principles of the present invention is shown in FIG. 1. FIG. 1 shows the positioning of an x-ray source 4 with primary radiation diaphragm 5, and an x-ray image intensifier 6 and video chain 7, provided for locating the calculus 3, in relation to a patient 2 on bed 1. To obtain spatial information concerning the position of the calculus 3, the x-ray system consisting of the components 4, 5, 6 can be pivoted around an axis 8 by an angle, alpha, such that a transradiation of the patient 2 from different directions is possible. The axis 8 should coincide with calculus 3. The bed 1 can be adjusted to provide for such coincidence.

Once the calculus 3 is located, it can be disintegrated by emitting shock waves focused onto a focal region, adjusted in coincidence with calculus 3. The shock wave head 9 has its application side covered by a flexible foil 11 that is applied to the surface of the patient 2 for acoustic coupling. The shock wave head 9 is attached to the primary radiation diaphragm 5 and may be adjusted in the direction of the central ray 10 of the x-ray system. Thus, adjustment can be achieved by individually adjusting the shock wave head 9 alone, or by adjusting both shock wave head 9 and the x-ray radiator 4.

The central ray 10 of the x-ray system proceeds roughly centrally through the shock wave head 9. This passage is achieved through a central, hollow-cylindrical space 12, which is air-filled, allowing for the unattenuated passage of x-rays. The hollow-cylindrical walls of the space 12 limit the space within the shock wave head 9 which is filled with coupling fluid. To locate the position of the calculus, an image must be obtained from two directions, separated by an angle alpha. For this purpose, the x-ray system consisting of the components 4, 5 and 6 may be mounted so as to be pivotable, or alternatively a second x-ray system (not shown), at angle alpha from the central ray 10, may be provided, which permits the x-ray system consisting of components 4, 5 and 6 to be stationarily mounted. The x-ray radiator 4 may also be employed to produce stereo x-ray images, in which case the x-ray radiator 4 will have two foci that radiate in alteration, and the central rays which emanate from these foci describe a small angle with each other. Such a configuration requires that the space 12 be dimensioned such that the x-ray beams emitted by the two foci completely penetrate the patient 2.

A second possible arrangement for the shock wave head 9 is indicated by dot-dash lines in FIG. 1, showing the shock wave head 9 disposed in front of the x-ray image intensifier 6. In this case, the x-ray beam suitable for imaging is also defined by the dimensions of space 12.

A cross-sectional view of the lithotripter, FIG. 2, shows a shock wave head 9, comprised of closed space 13 filled with coupling fluid. The application side is covered by a flexible foil 11 that is drawn over the space 12. The hollow-cylindrical walls of space 12 limit the space filled with the coupling fluid. An ultrasound applicator 14, which is part of a known ultrasound locating system including an ultrasound signal processing circuit 17 and a display 18, is disposed in the space 12.

Thus, no measures are necessary to prevent run out of the coupling fluid when the ultrasound applicator 14 is axially removed. A shock wave source 15 is arranged at the rear of the space 13.

The shock wave source 15, which may be piezoceramic or electro-dynamic, is provided for the shock wave head 9. It emits shock waves in a known manner which are focused by an acoustic lens system 16, that can be adjustable for varying the position of the focal region.

Although modifications and changes may be suggested by those skilled in the art, it is the intention of the inventors to embody within the patent warranted hereon all changes and modifications as reasonably and properly come within the scope of their contribution to the art.

We claim as our invention:

1. An extracorporeal lithotripsy apparatus comprising:
    means for generating shock waves adapted for non-invasive treatment of calculi in the body of a patient, said means for generating shock waves having a focus at which said shock waves converge;
    transmission means for transmitting shock waves from said means for generating shock waves, said transmission means including a propagation medium for said shock waves in a closed space and having an application surface formed by a flexible cover adapted for pressing against said patient to couple said shock waves into said patient, said transmission means having a central receptacle which is closed at an end by said application surface;
    means for generating a radiation field for locating the position of said calculus in said patient disposed behind said means for generating shock waves; and
    said receptacle being transmissive for said radiation field so that said radiation field is unattenuated by passage therethrough.

2. An extracorporeal lithotripsy apparatus comprising:
    means for generating shock waves adapted for non-invasive treatment of calculi in the body of a patient, said means for generating shock waves having a focus at which said shock waves converge;
    transmission means for transmitting shock waves from said means for generating shock waves, said transmission means including a propagation medium for said shock waves in a closed space and having an application surface formed by a flexible cover adapted for pressing against said patient to couple said shock waves into said patient, said transmission means having a central receptacle which is closed at an end by said application surface;
    means for generating a first radiation field for identifying the position of said calculus in said patient including a radiation source and a radiation receiver, said means for generating shock waves being disposed between said radiation source, and said radiation receiver, said receptacle being transmissive for said first radiation field so that said first radiation field is unattenuated by passage therethrough; and
    means for generating a second radiation field for identifying the position of said calculus in said patient, said means for generating a second radiation field including a radiation applicator disposed in said receptacle when said means for generating a first radiation field is not in use.

3. A lithotripsy apparatus as claimed in claim 2, wherein said radiation source is an x-ray source and wherein said radiation receiver is an x-ray receiver.

4. A lithotripsy apparatus as claimed in claim 2, wherein said means for generating a second radiation field comprises means for generating an ultrasound field.

* * * * *